(12) United States Patent
Groenland et al.

(10) Patent No.: US 12,171,598 B2
(45) Date of Patent: Dec. 24, 2024

(54) TEMPORARILY ATTACHMENT OF MEDICAL EQUIPMENT TO A SUBJECT SUPPORT

(71) Applicant: KONINKLIJKE PHILIPS N.V., Eindhoven (NL)

(72) Inventors: Alfons Wouter Groenland, Best (NL); Carl Rowe, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 203 days.

(21) Appl. No.: 17/800,907

(22) PCT Filed: Feb. 17, 2021

(86) PCT No.: PCT/EP2021/053907
§ 371 (c)(1),
(2) Date: Aug. 19, 2022

(87) PCT Pub. No.: WO2021/165331
PCT Pub. Date: Aug. 26, 2021

(65) Prior Publication Data
US 2023/0076054 A1    Mar. 9, 2023

Related U.S. Application Data

(60) Provisional application No. 62/978,494, filed on Feb. 19, 2020.

(30) Foreign Application Priority Data

Jul. 7, 2020  (EP) ..................... 20184372

(51) Int. Cl.
*A61B 6/04*   (2006.01)
*A61B 6/42*   (2024.01)

(52) U.S. Cl.
CPC .............. *A61B 6/0407* (2013.01); *A61B 6/42* (2013.01)

(58) Field of Classification Search
CPC ................................ A61B 6/0407; A61B 6/42
See application file for complete search history.

(56) References Cited

U.S. PATENT DOCUMENTS 3,840,221 A    10/1974  Hogan
3,981,492 A *  9/1976   Hallmann ............ A61B 6/0421
                                                     5/81.1 R (Continued)

FOREIGN PATENT DOCUMENTS

JP        1176225 A       3/1999
JP     2006109990 A       4/2006

(Continued)

OTHER PUBLICATIONS

International Search Report and Written Opinion of PCT/EP2021/053907, dated Apr. 28, 2021.

*Primary Examiner* — Blake C Riddick (57) ABSTRACT

The present invention relates to the arrangement of medical equipment during X-ray imaging. In order to provide further holding for medical equipment, a temporarily attachment of medical equipment to a subject support (26) is provided. A panel-like structure (12) is provided to be arranged between the structure of the subject support (32) and a covering mattress (34) or the like on which the subject is then arranged. An attachment interface (14) is provided at the edge of the panel, which interface can be used for a temporarily mount of the equipment. The attachment interface can be formed as a rail-segment. The panel is X-ray transparent to allow X-ray imaging of the subject from an increased range of directions. The attachment interface can be X-ray opaque or also X-ray transparent.

15 Claims, 3 Drawing Sheets

(56) References Cited

U.S. PATENT DOCUMENTS

| | | | | |
|---|---|---|---|---|
| 4,193,148 A * | 3/1980 | Rush | A61G | 1/0212 |
| | | | | 5/601 |
| 4,287,422 A * | 9/1981 | Kuphal | A61B | 6/0407 |
| | | | | 5/601 |
| 4,506,872 A | 3/1985 | Westerberg | | |
| 4,584,989 A * | 4/1986 | Stith | A61G | 7/0528 |
| | | | | 177/144 |
| 5,758,374 A * | 6/1998 | Ronci | A61G | 13/101 |
| | | | | 108/65 |
| 6,022,143 A * | 2/2000 | Helmreich | A61B | 6/00 |
| | | | | 378/195 |
| 6,325,538 B1 * | 12/2001 | Heesch | G21F | 3/00 |
| | | | | 250/517.1 |
| 6,366,799 B1 * | 4/2002 | Acker | A61B | 5/064 |
| | | | | 600/424 |
| 6,375,355 B1 * | 4/2002 | Fortin | A61B | 6/0442 |
| | | | | 5/624 |
| 6,632,170 B1 | 10/2003 | Bohanan | | |
| 6,944,897 B2 * | 9/2005 | Koch | A61G | 13/101 |
| | | | | 5/503.1 |
| 7,020,917 B1 * | 4/2006 | Kolody | A61G | 13/101 |
| | | | | 5/601 |
| 7,913,337 B1 * | 3/2011 | Masson | A61G | 1/0212 |
| | | | | 5/942 |
| 2002/0078504 A1 | 6/2002 | Zitzmann | | |
| 2002/0138904 A1 * | 10/2002 | Wong | A61G | 7/012 |
| | | | | 5/713 |
| 2003/0061660 A1 * | 4/2003 | Easterling | F16M | 13/022 |
| | | | | 5/600 |
| 2003/0205176 A1 * | 11/2003 | Kolody | A61G | 13/101 |
| | | | | 108/28 |
| 2004/0088793 A1 | 5/2004 | Koch | | |
| 2005/0166325 A1 * | 8/2005 | Tidwell | A61G | 13/12 |
| | | | | 5/624 |
| 2006/0016006 A1 * | 1/2006 | Whitmore, III | A61B | 5/704 |
| | | | | 5/601 |
| 2007/0094798 A1 * | 5/2007 | Yu | A61G | 13/10 |
| | | | | 5/507.1 |
| 2007/0129634 A1 * | 6/2007 | Hickey | F16M | 13/027 |
| | | | | 600/439 |
| 2008/0031422 A1 * | 2/2008 | Barkow | A61B | 6/107 |
| | | | | 378/203 |
| 2009/0212535 A1 * | 8/2009 | Darling, III | B62B | 13/18 |
| | | | | 280/651 |
| 2010/0071128 A1 * | 3/2010 | Campagna | A61G | 13/0045 |
| | | | | 5/81.1 R |
| 2011/0103555 A1 * | 5/2011 | Hunt | A61B | 6/107 |
| | | | | 378/203 |
| 2011/0231996 A1 * | 9/2011 | Lemire | A61G | 7/052 |
| | | | | 5/613 |
| 2014/0083436 A1 * | 3/2014 | Pettinato | A61G | 13/101 |
| | | | | 128/870 |
| 2015/0272803 A1 | 10/2015 | Wyslucha | | |
| 2016/0158082 A1 * | 6/2016 | Gainor | A61B | 6/0407 |
| 2016/0213543 A1 * | 7/2016 | Hafner | A61G | 13/1205 |
| 2016/0235376 A1 * | 8/2016 | Kaiser | A61G | 13/123 |
| 2016/0242708 A1 * | 8/2016 | Kaiser | A61G | 13/122 |
| 2017/0119324 A1 * | 5/2017 | Wilson | G21F | 3/00 |
| 2018/0337018 A1 * | 11/2018 | Adachi | G03B | 42/025 |
| 2018/0353144 A1 * | 12/2018 | Stoutenburgh | A61B | 6/0407 |
| 2019/0246995 A1 * | 8/2019 | Egolf | A61B | 6/44 |
| 2020/0022860 A1 * | 1/2020 | Van Doorn | A61B | 90/57 |
| 2020/0046304 A1 * | 2/2020 | Saito | A61B | 6/0407 |
| 2020/0093446 A1 * | 3/2020 | Wilson | A61B | 6/0442 |
| 2020/0214639 A1 * | 7/2020 | Germaneau | A61B | 6/0421 |
| 2020/0253686 A1 * | 8/2020 | Krause | A61B | 17/8897 |
| 2020/0397389 A1 * | 12/2020 | Stoutenburgh | A61B | 6/0407 |
| 2021/0059620 A1 * | 3/2021 | Ortega Jimenez | A61B | 6/487 |

FOREIGN PATENT DOCUMENTS

| | | |
|---|---|---|
| WO | 200230285 A2 | 4/2002 |
| WO | 2018146026 A1 | 8/2018 |

* cited by examiner

TEMPORARILY ATTACHMENT OF MEDICAL EQUIPMENT TO A SUBJECT SUPPORT

CROSS-REFERENCE TO PRIOR APPLICATIONS

This application is the U.S. National Phase application under 35 U.S.C. § 371 of International Application No. PCT/EP2021/053907, filed on Feb. 17, 2021, which claims the benefit of U.S. Provisional Patent Application No. 62/978,494, filed on Feb. 19, 2020 and European Patent Application No. 20184372.9, filed on Jul. 7, 2020. These applications are hereby incorporated by reference herein.

FIELD OF THE INVENTION

The present invention relates to the arrangement of medical equipment during X-ray imaging, and relates in particular to an attachment device for a subject support in medical X-ray imaging, to an X-ray imaging system and to a method for providing attachment interface for temporal attachment of medical equipment at a subject support during X-ray imaging.

BACKGROUND OF THE INVENTION

During interventions in a cathlab, medical X-ray imaging is used for various purposes, like guiding during an intervention, i.e. intra-operative, or as pre-operative imaging. X-ray imaging is also used for assessing an outcome or an interim step during an operation. During interventions in a cathlab, for example, also intravascular ultrasound (IVUS) catheters and wires for fractional flow reserve (FFR) and instantaneous wave-free ratio (iFR) measurements may be used. These catheters and wires electrically may interface with a patient interface module (PIM) that connects with a cable to a console. PIMs can be attached with a clamp to a rail of the surgical table in a cathlab. However, the table rail may not be present at all sides of the table. US 2004 088793 A1 relates to an arrangement for holding accessory parts to a patient support surface.

SUMMARY OF THE INVENTION

There may thus be a need to provide further holding for medical equipment.

The object of the present invention is solved by the subject-matter of the independent claims; further embodiments are incorporated in the dependent claims. It should be noted that the following described aspects of the invention apply also for the attachment device for a subject support in medical X-ray imaging, for the X-ray imaging system and for the method for providing an attachment interface for temporal attachment of medical equipment at a subject support during X-ray imaging.

According to the present invention, an attachment device for a subject support in medical X-ray imaging is provided. The device comprises a holding panel structure and an accessory rail connector. The accessory rail connector is configured as an attachment interface for temporal attachment of medical equipment at a subject support during X-ray imaging. The holding panel structure comprises a flat body with a first surface on a first side and a second surface on a second side. The first surface is configured to abut against a first load bearing support surface and the second surface is configured to abut against a second load bearing support surface, wherein moreover the flat body is configured to be secured between the first and second load bearing support surfaces by a load being present on the subject support. The first surface and the second surface of the flat body are facing in opposite directions. Further, the accessory rail connector is mechanically connected to the holding panel structure. Still further, at least a part of the holding panel structure is X-ray transparent.

This provides the effect that a section of table rail can be offered or provided all around a subject support, in particular where there is no fixed table rail present. The flat body of the holding panel structure, for example a relatively thin panel, can be slid temporarily under the patient and the mattress. In this position, the panel is secured between the load bearing support surfaces when a load is present on top of the subject support, such as the weight of a patient positioned on top of a mattress or cushion placed on a patient support top side. Being potentially in the X-ray beam, the panel is designed to be radio transparent to avoid influencing the X-ray image quality.

The subject support can thus be provided without, or at least with less rail segments arranged around its edges.

According to an example, the holding panel structure is provided as a holding panel, and at least a central portion of the holding panel is made from an X-ray transparent material.

In an alternative example, the flat body structure of the holding panel structure is provided as a holding frame with at least two lateral frame segments, and e.g. an empty middle or central portion between them.

The two frame segments may also have a connecting edge frame segment on the side where the accessory rail connector is provided.

The two frame segments may in addition also have a connecting edge frame segment on the side opposite where the accessory rail connector is provided.

The frame segments form the first surface and the second surface.

In the following, the holding panel structure can also be referred to as holding panel.

According to an example, the holding panel structure is configured to provide a temporary mounting of the attachment device to the subject support in a one-hand operation. In other words, the attachment device may advantageously be attached to, and detached from, the subject support, using only one (free) hand.

According to an example, the holding panel structure and the accessory rail connector are configured to provide a clamp-free attachment device.

According to an example, the holding panel structure provides a single-mount of the attachment device.

According to an example, the holding panel structure comprises a flat panel at its first end, the panel being configured to be secured between two support surfaces of a subject support by an external load placed on the subject support. Further, the accessory rail connector is mechanically connected to the holding panel structure in a connecting region arranged on a second end, which is opposite to the first end.

According to an example, the flat body structure is dimensioned such that it is secured between the load bearing support surfaces when an external load is present on the subject support and while medical equipment is temporarily attached to the rail connector.

According to an example, the holding panel structure is provided as a flat insertion part configured to be inserted between an upper rigid subject support surface and a cushion cover. In this example, the external load may be a patient resting on top of the cushion cover of the patient support during a medical procedure, and the flat insertion panel is dimensioned such that it is properly held in place by the weight of the patient while medical equipment is temporarily attached to the rail connector. For example, the flat insertion part can easily be slid under the mattress of the patient support when a patient is resting on top of it, whereby the attachment device becomes secured between the load bearing support surfaces by the patient's weight.

According to an example, the accessory rail connector and the holding panel structure are permanently connected.

According to the present invention, also an X-ray imaging system is provided. The system comprises an X-ray imaging device with an X-ray source and an X-ray detector. The system further comprises a subject support with an upper table structure surface and a subject support surface arranged on top of the table structure surface. The system still further comprises an attachment device according to one of the preceding examples. For a temporary mount, the holding panel structure is at least partly arranged between the upper table structure surface and the subject support surface such that the accessory rail connector provides an attachment interface for temporal attachment of medical equipment at a subject support during X-ray imaging.

According to the present invention, also a method for temporarily attaching medical equipment to a subject support during X-ray imaging is provided. The method comprises the following steps:

in a first step, providing an attachment device with a holding panel structure that has a flat body and an accessory rail connector being mechanically connected to the holding panel structure and being configured as an attachment interface for temporal attachment of medical equipment at a subject support during X-ray imaging. At least a part of the holding panel structure is X-ray transparent.

In a second step, securing the holding panel structure between a first load bearing support surface of the subject support and a second load bearing support surface of the subject support while a load is present on the subject support.

According to an aspect, a temporarily attachment of medical equipment to a subject support is provided. A panel-like structure is provided to be arranged between a structure of the subject support and a covering mattress or the like on which the subject is then arranged. An attachment interface is provided at the edge of the panel, which interface can be used for a temporarily mount of the equipment. The attachment interface can be formed as a rail-segment. The panel is X-ray transparent to allow X-ray imaging of the subject from an increased range of directions. The attachment interface can be X-ray opaque or also X-ray transparent.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Certain embodiments will now be described in greater details with reference to the accompanying drawings. In the following description, like drawing reference numerals are used for like elements, even in different drawings. The matters defined in the description, such as detailed construction and elements, are provided to assist in a comprehensive understanding of the exemplary embodiments. Also, well-known functions or constructions are not described in detail since they would obscure the embodiments with unnecessary detail. Moreover, expressions such as "at least one of", when preceding a list of elements, modify the entire list of elements and do not modify the individual elements of the list.

The term "subject" may also be referred to as individual. The subject may further also be referred to as patient, although it is noted that this term does not indicate whether any illness or disease is actually present with the subject.

In intervention guided therapy, catheters may be inserted into arteries of the human body and pushed to the proper location in the human body by the physician, for example for coronary or peripheral interventions in cathlabs. Besides the fixed, integrated, systems, there are also 'mobile' cart-based solutions, which do not have the under-the-floor cable, but rather a direct connection from patient bed to the mobile cart-based PC. The clinical context for the use of the catheters and wires is those parts of the body suffer from limited oxygenation due to limited blood flow. This could be the heart ('coronary'), but also limbs ('peripheral') or organs. The limited blood flow may be caused by local narrowing of the blood vessel ('stenosis') and diagnosis and treatment aim at identification and removal of the stenosis. Classis diagnosis and treatment may be done under X-ray, but is limited due to the 3D nature of the problem in combination with 2D imaging. Furthermore, a contrast agent must be added to the blood stream to visualize vessels, which can be harmful to the patient. In addition, the general trend is to minimize the applied X-ray dose for the health of both the patient and the physician. The intravascular ultrasound (IVUS) and FM (FFR/iFR) modalities allow the physician to reduce the use of X-ray while getting to the diagnosis.

The system consists of a sterile and disposable guidewire or catheter to do measurements from within the vessel of pressure (FFR/iFR) or to image with ultrasound (IVUS). The disposables are connected to a box, i.e. the patient interface module (PIM) at the table edge from where it is electrically interfaced with the rest of the system. The PIMs themselves may be attached to the rail with a holster with a clamp.

As cable length of disposables may be limited, the PIM, in accordance herewith, can advantageously be arranged closely to the vessel access point. This holds true not only for the classic femoral access, but also for the increasingly more popular radial access sites (lower complication risk) as well as so-called brachial and jugular access sites, which are used especially for peripheral interventions.

By mounting the attachment device via the holding panel structure anywhere along the table's edge, an attachment rail can be made available on the complete surface area of the table, not only in proximity of the lower half of the body. Also, for hybrid operation room tables, the rail space is no longer limited to the table controls only. For an office based lab (OBL) table, when no rail available at all, the attachment device provides this option of a rail.

Thus, the attachment device provides for flexible and temporary mouting of medical equipment such as a PIM, thereby avoiding that such equipment has to be bagged and placed in the sterile field onto the patient. Hence, the attachment device provides convenience, and means less workflow interruption. The temporarily attached rail acts as mechanical anchor for the PIM. In case someone steps on the cable between the PIM and console, the anchor function prevents possible rupture of the catheter access site.

In another example, the equipment to be mounted temporarily to the attachment device may be a touch-screen module (TSM). TSM devices may for example be used in the cathlab for controlling X-ray imaging parameters, viewing acquired X-ray images and/or setting X-ray collimation devices such as shutters and wedges. By mounting a TSM by means of an attachment device as disclosed herein, the TSM device can be quickly mounted to the subject support by sliding the flat panel of the attachment device between the load bearing support surfaces when needed. Thus, the TSM placement can be done in a flexible manner along the edges of the patient support, whereby the TSM can be optimally positioned within the field of view of the physician irrespective of the vessel access point at which the physician is present.

Furthermore, the TSM may be easily removed during parts of the procedure when optimal patient access, unhindered by the presence of the relatively bulky TSM, is required.

The X-ray translucent panel is not influencing in X-ray image and by being sufficiently thin (few mm) it does not impact the comfort of the patient on the table. The rail may have the dimensions of the table rail, but can be made from the same material as the panel (one part). The surface area of the panel is large enough that the panel stays in place, in any case in the presence of a load on the subject support such as a subject on the table while medical equipment is temporarily mounted to the attachment rail. For example, the panel may have a width (being a dimension in a longitudinal or "long" direction of a patient support) of 150 mm and a height (being a dimension in a transverse or "short" direction of a patient support of 400 mm After use, the panel is stored and can be cleaned easily. Since the attachment device may be arranged outside the sterile field, same rules and regulations apply as for the PIM and other rail mounted devices. Use of the device can be, but not limited to, the mounting of IVUS/FFR PIMs, or the mounting of touch-screen modules (TSMs) such as described in the above.

Figure 1:
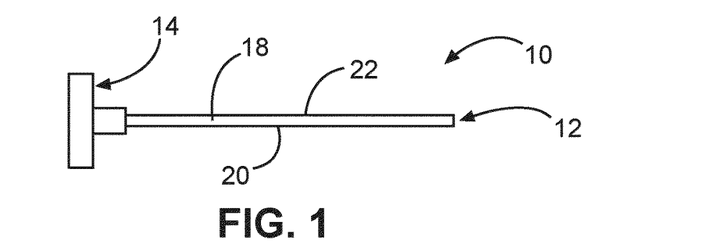
FIG. 1 schematically shows a cross section of an example of an attachment device for a subject support in medical X-ray imaging.

FIG. 1 schematically shows a cross section of an example of an attachment device 10 for a subject support in medical X-ray imaging. The attachment device 10 comprises a holding panel structure 12 and an accessory rail connector 14. The accessory rail connector 14 is configured as an attachment interface 16 for temporal attachment of medical equipment at a subject support during X-ray imaging. The holding panel structure 12 comprises a flat body 18 with a first surface 20 on a first side and a second surface 22 on a second side. The first surface 20 is configured to abut against a first load bearing support surface (see FIG. 2) and the second surface 22 is configured to abut against a second load bearing support surface (see FIG. 2), such that the flat body is secured between the first and second load bearing support surfaces. The first surface 20 and the second surface 22 are each facing in opposite directions. The accessory rail connector 14 is mechanically connected to the holding panel structure 12. At least a part of the holding panel structure 12 is X-ray transparent.

For example, a central area is X-ray transparent.

The term "X-ray transparent" relates to an X-ray attenuation behavior that is low enough to be hardly or even invisible on an X-ray image made from a subject in an area in which the holding panel structure is arranged. The term "X-ray transparent" is also referred to as X-ray translucent.

In an option, as shown in FIG. 1, the holding panel structure is provided as a holding panel, and wherein at least a central portion of the holding panel is made from an X-ray transparent material.

In an alternative example, not shown, the flat body structure of the holding panel structure is provided as a holding frame with at least two lateral frame segments.

The frame parts can be X-ray-non-transparent, e.g. X-ray opaque, whereas the (open or empty) middle or center portion is X-ray transparent.

Figure 2:
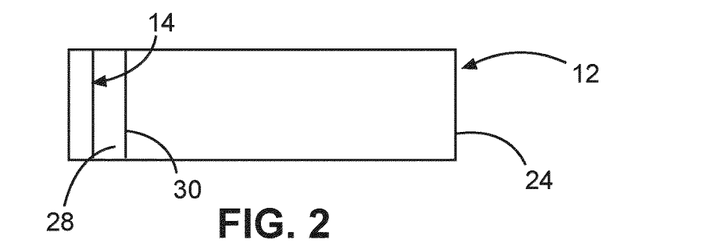
FIG. 2 schematically shows a top view of the example of FIG. 1.

FIG. 2 schematically shows a top view of the example of FIG. 1.

The accessory rail connector 14 is also referred to as accessory connector or accessory mount.

In an example, the attachment device 10 consists of the holding panel structure and the accessory rail connector. In other words, the attachment device does only comprise these two (functional) elements.

In an option, the holding panel structure 12 is configured to provide a temporary mount of the attachment device 10 to a subject support in a one-hand operation.

The term "one-hand operation" relates a mounting and removing (or dismantling) procedure that requires only one hand, i.e. that can be done by using one hand only. The one-hand operation is also referred to as single-hand operation.

In an example, a single-person mount is provided, by sliding the plate between top of the support structure and a mattress of the subject support. This may be done even in the presence of a patient on the mattress.

In an example, a single-person mount is provided, by lifting the mattress and positioning the plate, followed by putting back the mattress.

In an option, the holding panel structure 12 and the accessory rail connector 14 are configured to provide a clamp-free attachment device.

The holding panel structure 12 and the accessory rail connector 14 are provided as additional-clamp-free components. In an option, the attachment device 10 is free of any further (additional) clamping or mounting elements. The holding panel structure 12 provides the complete mounting. The attachment device 10 is thus provided to be clamp-free. The attachment device 10 is free of any auxiliary or secondary holding devices/elements.

In an option, the holding panel structure 12 provides a single-mount of the attachment device 10.

Figure 3:
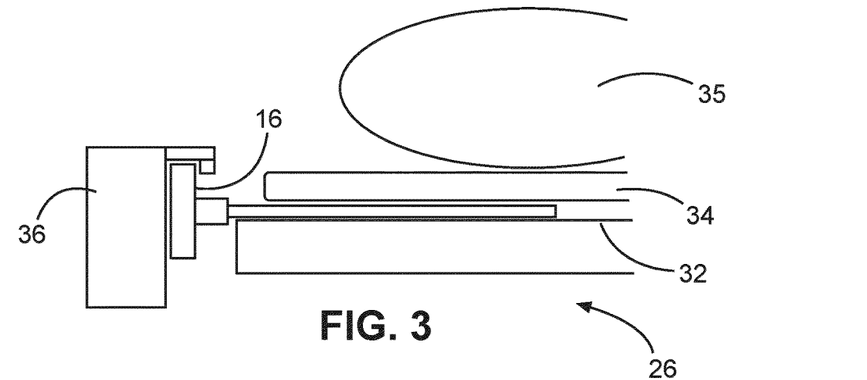
FIG. 3 schematically shows a cross section of an attachment device temporarily mounted to a subject support.
Figure 4:
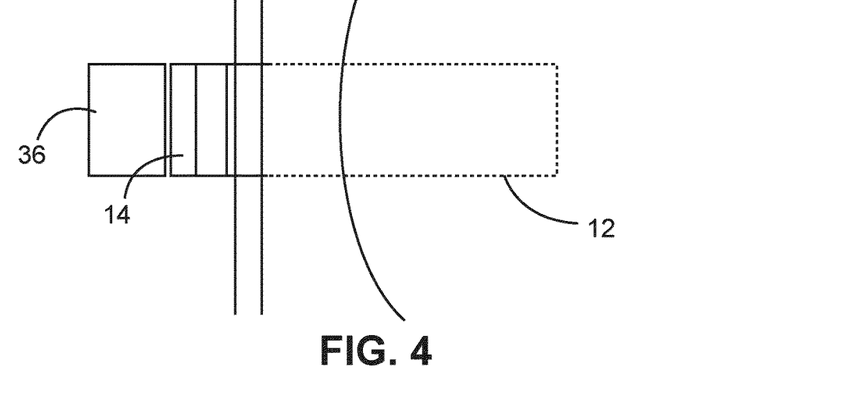
FIG. 4 schematically shows a top view of the example of FIG. 3.

Besides the holding panel structure, no other support or mounting means are provided. The single-mount can also be referred to as only-mount or one-piece mount. As indicated in FIG. 3 and FIG. 4, in an option, the holding panel structure 12 comprises a first end 24 configured to be arranged between two support surfaces of a subject support 26. The accessory rail connector 14 is mechanically connected to the holding panel structure 12 in a connecting region 28 arranged on a second end 30, which is opposite to the first end. The first end 24 is also referred to as free end or front end. The second end 30 is also referred to as connecting end or back end.

In an example, the accessory rail connector 14 is mechanically connected to the holding panel structure 12 in a connecting region. The holding panel structure 12 is X-ray transparent at least in an area that is opposite to the connecting region.

In an option, the holding panel structure 12 is provided as a flat insertion part configured to be secured between an upper rigid subject support surface 32 and a cushion cover 34 while a load is present on the subject support 26

In an example, the flat insertion part has a height (or thickness) in the range of below 20 mm, preferably below 10 mm.

In an example, the flat insertion part is dimensioned such that it is properly held in place when a patient is present on a top surface of the support and while medical equipment is temporarily attached to the rail connector. For example, the panel may have a height in the range of 300 mm to 500 mm, for example, 400 mmFurther, the flat insertion part may have a width in the range of 100 mm to 300 mm, for example, 150 or 200 mm.

FIG. 3 schematically shows a cross section of the attachment device 10 temporarily mounted to the subject support 26. The holding panel structure 12 is arranged on top of the upper rigid subject support surface 32, i.e. on the tabletop, and below the cushion cover 34 and extends to the left side in the drawing providing the accessory rail connector 14. A subject 35 is arranged on the cushion cover 34. As an example, a patient interface module 36 is attached to the accessory rail connector 14.

In FIG. 4, a top view of the example of FIG. 3 is shown. The holding panel structure 12 is arranged below the cushion cover 34 and extends on the side providing the accessory rail connector 14, to which the patient interface module 36 is attached.

In an option, as also shown in FIG. 3, FIG. 4 and FIGS. 5A, 5B and 5A, for a mounting of the attachment device 10 to the subject support 26, the holding panel structure 12 is configured to be insertable between the upper rigid subject support surface 32 and the cushion cover 34 of the subject support 26.

In an example, the holding panel structure 12 is configured to be arranged between a table structure surface of a subject support and a subject support surface arranged on top of the table structure surface.

In an option, the accessory rail connector 14 and the holding panel structure 12 are permanently connected.

In an option, the accessory rail connector 14 and the holding panel structure 12 are made as one-piece.

In an option, the attachment device 10 comprises a hybrid construction: The holding panel structure 12 comprises a first, radio-transparent material, and the accessory rail connector 14 comprises a second material that is different than the first material.

In an option, the second material is radio-opaque.

In an option, the accessory rail connector 14 and the holding panel structure 12 are both X-ray transparent. In another option, the accessory rail connector 14 and the holding panel structure 12 are made of the same material.

A manufacturing process for this device (single material, one part) may be casting of an X-ray translucent polymer.

In an option, the accessory rail connector 14 is configured to provide a substitute rail on an edge of a subject support table. The substitute rail can also be referred to as auxiliary rail, replacement rail or subsidiary rail.

In an example, the accessory rail connector comprises a rail segment with a cross section having an upper part for an overlapping hanging portion of a mount of a medical equipment and a front part for an abutting of a support portion of the mount of the medical equipment.

The attachment interface can also be referred as a "mounting rail", "attachment rail" or "rail".

Figure 5A:
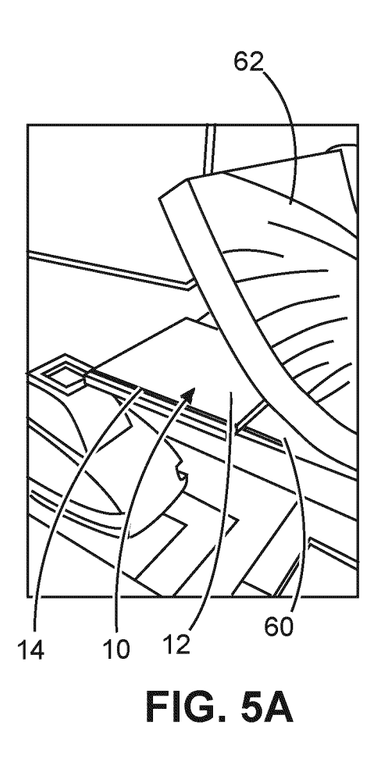
FIGS. 5A, 5B and 5C show views of the attachment device and the support structure in the context of an X-ray imaging system.
Figure 5B:
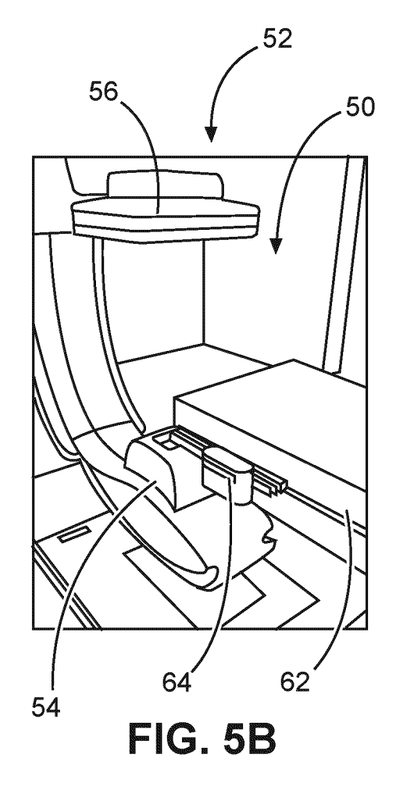
Figure 5C:
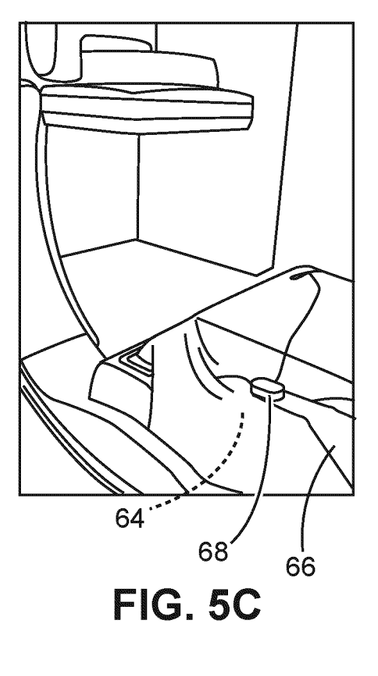

FIGS. 5A, 5B and 5C show views of the attachment device and the support structure in the context of an X-ray imaging system 50. In an option, the X-ray imaging system 50 comprises an X-ray imaging device 52 with an X-ray source 54 and an X-ray detector 56. Further, the X-ray imaging system 50 comprises a subject support 58 with an upper table structure surface 60 and a subject support surface 62 arranged on top of the table structure surface. Still further, the X-ray imaging system 50 comprises an example of the attachment device 10 according to one of the preceding examples. For a temporary mount, the holding panel structure is at least partly secured between the upper table structure surface 60 and the subject support surface 62 such that the accessory rail connector 14 provides an attachment interface for temporal attachment of medical equipment at the subject support during X-ray imaging.

In an example, the subject support surface 62 is a mattress.

In an example, a patient interface module, PIM, 64 is temporarily attached to the accessory rail connector 14 during the X-ray imaging. In another example, a touch screen module is temporarily attached to the accessory rail connector 14 during the X-ray imaging.

FIG. 5A shows the subject support surface 62, i.e. the mattress, being lifted and the holding panel structure 12 is arranged on the upper table structure surface 60, i.e. on the rigid part of the subject support. The accessory rail connector 14 is provided near a side region of the subject support.

FIG. 5B shows the subject support surface 62, i.e. the mattress, being lowered again, thus holding the holding panel structure 12 between the table structure and the mattress. The patient interface module 64 is attached to the accessory rail connector 14.

FIG. 5C shows the arrangement ready for use in an intervention. The subject support surface 62 is covered by a cloth 66 or drape, for example a sterile cloth. The patient interface module 64 can be covered by cloth 66.

Figure 6:
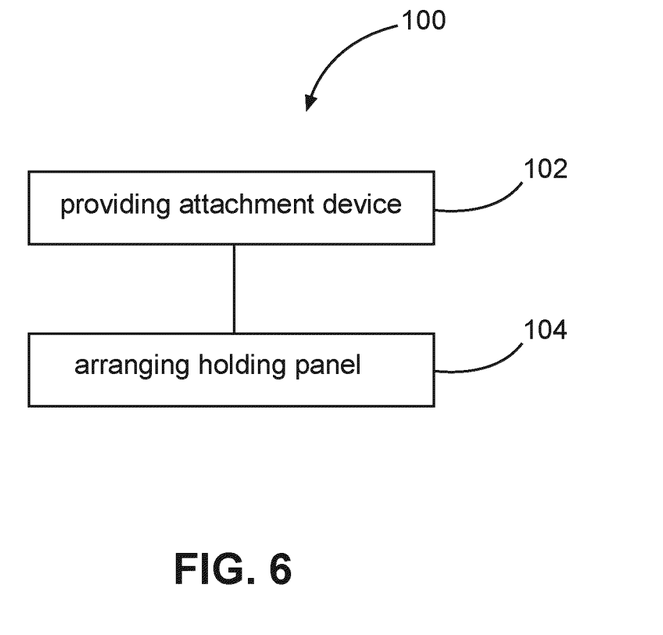
FIG. 6 shows steps of an example of a method for providing an attachment interface for temporal attachment of medical equipment at a subject support during X-ray imaging.

FIG. 6 shows steps of an example of a method 100 for temporarily attaching medical equipment to a subject support during X-ray imaging. The method 100 comprises the following steps:

In a first step 102, also referred to as step a), an attachment device is provided. The attachment device comprises a holding panel structure having a flat body and an accessory rail connector being mechanically connected to the holding panel structure and being configured as an attachment interface for temporal attachment of medical equipment at a subject support during X-ray imaging. At least a part of the holding panel structure is X-ray transparent.

In a second step 104, also referred to as step b), the holding panel structure is secured between a first load bearing support surface of the subject support and a second load bearing support surface of the subject support while a load is present on the subject support.

Following, the accessory rail connector can be used for mounting of medical equipment (not shown in FIG. 6).

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated, and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An attachment device for a subject support in medical X-ray imaging, the device comprising:
    a holding panel structure; and
    an accessory rail connector;
    wherein the accessory rail connector is configured as an attachment interface for temporal attachment of medical equipment at the subject support during the medical X-ray imaging;
    wherein the holding panel structure comprises a flat body structure with a first surface on a first side and a second surface on a second side, the first surface and the second surface each facing in opposite directions,
    wherein the first surface is configured to abut against a first load bearing support surface and the second surface is configured to abut against a second load bearing support surface, and wherein the flat body is configured to be secured between the first and second load bearing support surfaces by a load being present on the subject support;
    wherein the accessory rail connector is mechanically connected to the holding panel structure; and
    wherein at least a part of the holding panel structure is X-ray transparent.

2. The attachment device according to claim 1, wherein the holding panel structure is provided as a holding panel, and wherein at least a central portion of the holding panel is made from an X-ray transparent material.

3. The attachment device according to claim 1, wherein the holding panel structure is configured to provide a temporary mounting of the attachment device to the subject support in a one-hand operation.

4. The attachment device according to claim 1, wherein the holding panel structure and the accessory rail connector are configured to provide a clamp-free attachment device.

5. The attachment device according to claim 1, wherein the holding panel structure provides a single-mount of the attachment device.

6. The attachment device according to claim 1, wherein the holding panel structure comprises a flat panel at its first end, the panel being configured to be secured between two support surfaces of a subject support by an external load placed on the subject support; and
    wherein the accessory rail connector is mechanically connected to the holding panel structure in a connecting region arranged on a second end, which is opposite to the first end.

7. The attachment device according to claim 1, wherein the holding panel structure is provided as a flat insertion part configured to be inserted between an upper rigid subject support surface and a cushion cover.

8. The attachment device according to claim 1, wherein the flat body structure is dimensioned such that it is secured between the load bearing support surfaces when an external load is present on the subject support and while medical equipment is temporarily attached to the rail connector.

9. The attachment device according to claim 1, wherein the accessory rail connector and the holding panel structure are permanently connected.

10. The attachment device according to claim 1, wherein the accessory rail connector and the holding panel structure are made as one-piece.

11. The attachment device according to claim 10, wherein the attachment device comprises a hybrid construction, wherein the holding panel structure comprises a first, radio-transparent material, and the accessory rail connector comprises a second material that is different than the first material.

12. The attachment device according to claim 1, wherein the accessory rail connector is configured to provide a substitute rail on an edge of a subject support table.

13. An X-ray imaging system comprising:
    an X-ray imaging device with an X-ray source and an X-ray detector;
    a subject support with an upper table structure surface and a subject support surface arranged on top of the table structure surface; and
    the attachment device according to claim 1;
    wherein, for a temporary mount, the holding panel structure is at least partly secured between the upper table structure surface and the subject support surface such that the accessory rail connector provides an attachment interface for temporal attachment of medical equipment at a subject support during X-ray imaging.

14. The X-ray imaging system of claim 13, further comprising medical equipment to be temporarily attached to the subject support, wherein the medical equipment comprises a patient interface module (PIM) or a touch screen module (TSM).

15. A method for temporarily attaching medical equipment to a subject support during X-ray imaging, the method comprising:
    providing an attachment device with a holding panel structure having a flat body and an accessory rail connector being mechanically connected to the holding panel structure and being configured as an attachment interface for temporal attachment of medical equipment at the subject support during the X-ray imaging;
    wherein at least a part of the holding panel structure is X-ray transparent; and securing the holding panel structure between a first load bearing support surface of the subject support and a second load bearing support surface of the subject support while a load is present on the subject support.

* * * * *